(12) United States Patent
Haddada et al.

(10) Patent No.: US 6,294,377 B1
(45) Date of Patent: Sep. 25, 2001

(54) ADENOVIRAL VECTORS OF CANINE ORIGIN

(75) Inventors: Hedi Haddada, Alfortville; Bernard Klonjkowski, Bondy; Michel Perricaudet, Ecrosnes; Emmanuelle Vigne, Ivry sur Seine, all of (FR)

(73) Assignee: Rhone-Poulenc Rorer SA, Antony Cedex (FR)

( * ) Notice: Subject to any disclaimer, the term of this patent is extended or adjusted under 35 U.S.C. 154(b) by 0 days.

(21) Appl. No.: 08/553,317

(22) PCT Filed: May 6, 1994

(86) PCT No.: PCT/FR94/00531

§ 371 Date: Nov. 29, 1995

§ 102(e) Date: Nov. 29, 1995

(87) PCT Pub. No.: WO94/26914

PCT Pub. Date: Nov. 24, 1994

(30) Foreign Application Priority Data

May 18, 1993 (FR) .................................. 93 05954

(51) Int. Cl.⁷ .............................. C12N 7/01; C12N 15/86
(52) U.S. Cl. .................................... 435/320.1; 435/172.3; 435/69.1; 435/325; 424/93.2; 514/44
(58) Field of Search ............................. 435/320.1, 172.3, 435/172.1, 240.2, 240.1, 252.3; 424/93.21, 93.2; 514/44; 536/22.1, 23.1

(56) References Cited

U.S. PATENT DOCUMENTS 4,920,209 * 4/1990 Davis .................................. 435/235

FOREIGN PATENT DOCUMENTS

9104316 * 4/1991 (WO) .
9111525 * 8/1991 (WO) .
9306223 * 4/1993 (WO) .
9319191 * 9/1993 (WO) .

OTHER PUBLICATIONS

Wigand et al., "Classification and epidemiology of adenoviruses", in Doerfler (ed.), Adenovirus DNA, Martinus Nijhoff Publ., Boston, MA, pp. 409–441, 1986.*
Grunhaus et al., Adenoviruses as Cloning Vectors, Virology, 3, 237–252 (1992).
Ballay et al EMBO J 4(13B):3861, 1985.*
Leyrero et al Gene 101: 195, 1991.*
Bajoccn et al Nature Genetics 3: 229, 1993.*
Berkner et al Current Topics in Microbiol & Immunology 158: 39, 1992.*
Rosenfeld et al Cell 68: 143, 1992.*
Stratford–Perricaudet et al HGT 219:51, 1991.*
Gluzman in Eukaryotic Viral Vectors , CSH, 1982, p187–192.*
ATCC Catalog, 1990, pp. 1–17.*
Marshall, Science, 269 :1050–1055, 1995.*
Miller et al., FASEB J., 9:190–199, 1995.*
Culver et al., TIG, 10(5), 174–178, 1994.*
Hodgson, Exp. Opin. Ther. Pat., 5(5): 459–468, 1995.*

* cited by examiner

*Primary Examiner*—Bruce R. Campell
*Assistant Examiner*—Scott D. Priebe

(57) ABSTRACT

The present invention resides in use of a recombinant adenovirus of animal origin containing a heterologous DNA sequence for the preparation of a pharmaceutical composition intended for the therapeutic and/or surgical treatment of the human body.

6 Claims, 5 Drawing Sheets

Figures 1, 2A:
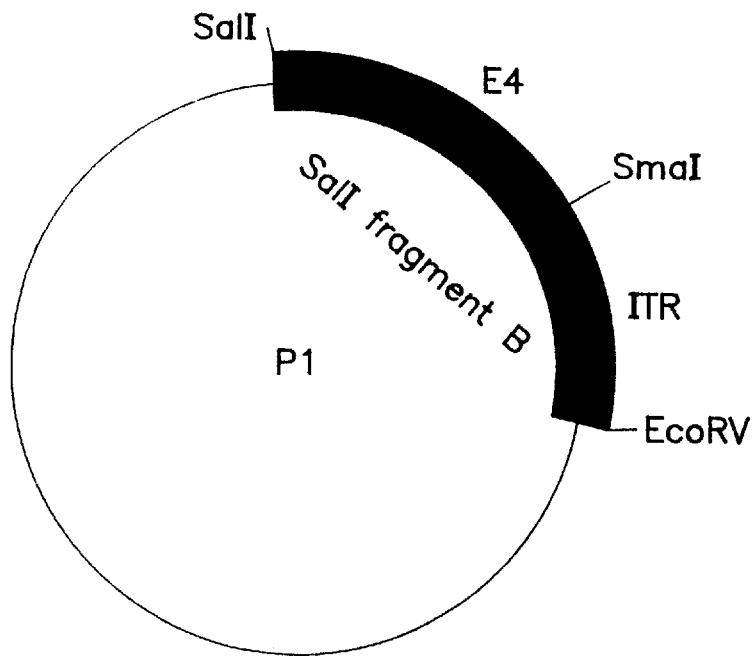

```
C  J K        A         G    E   I F        B        D         H
─┴──┴┴┴───────┴─────────┴────┴───┴┴┴────────┴────────┴─────────┴── Pst I

A                                   B
──────────────────────────────────────────────────────────┴─────── Sal I

I     C      E      F   G H     A          B        D   J
──┴─────┴──────┴──────┴───┴┴┴─────┴──────────┴────────┴───┴─────── Sma I
```

FIG. 1

Ligation of CAV2 and p2 digested with SalI

Transfection into MDCK

ADENOVIRAL VECTORS OF CANINE ORIGIN

This application is a national stage application filed under 35 USC 371 of PCT/FR94/00531 filed May 6, 1994.

The present invention relates to new viral vectors, to their preparation and to their use in gene therapy. It also relates to pharmaceutical compositions containing the said viral vectors. More especially, the present invention relates to the use of recombinant adenoviruses of animal origin as vectors for gene therapy.

Gene therapy consists in correcting a deficiency or an abnormality (mutation, aberrant expression, and the like) by introducing genetic information into the cell or organ affected. This genetic information may be introduced either in vitro into a cell extracted from the organ, the modified cell then being reintroduced into the body, or directly in vivo into the appropriate tissue. In this second place, different techniques exist, including various techniques of transfection involving complexes of DNA and DEAE-dextran (Pagano et al., J. Virol. 1 (1967) 891), of DNA and nuclear proteins (Kaneda et al., Science 243 (1989) 375) and of DNA and lipids (Felgner et al., PNAS 84 (1987) 7413), the use of liposomes (Fraley et al., J. Biol. Chem. 255 (1980) 10431), and the like. More recently, the use of viruses as vectors for gene transfer has been seen to be a promising alternative to these physical transfection techniques. In this connection, different viruses have been tested for their capacity to infect certain cell populations. This applies especially to retroviruses (RSV, HMS, MMS, and the like), the HSV virus, adeno-associated viruses and adenoviruses.

Among these viruses, the adenoviruses display certain properties which are advantageous for use in gene therapy. In particular, they have a fairly broad host range, are capable of infecting resting cells and do not integrate in the genome of the infected cell. For these reasons, adenoviruses have already been used for in vivo gene transfer. To this end, different vectors derived from adenoviruses have been prepared, incorporating different genes (β-gal, OTC, α-1AT, cytokines, and the like). All the vectors derived from the adenoviruses described in the prior art for the purposes of use in gene therapy in humans have hitherto been prepared from adenoviruses of human origin. These appeared, in effect, to be the most suitable for such a use. To limit the risks of multiplication and the formation of infectious particles in vivo, the adenoviruses used are generally modified so as to render them incapable of replication in the infected cell. Thus, the constructions described in the prior art are adenoviruses from which the E1 (E1a and/or E1b) and, where appropriate, E3 regions have been deleted, at the site of which regions sequences of interest are inserted (Levrero et al., Gene 101 (1991) 195; Gosh-Choudhury et al., Gene 50 (1986) 161). However, in addition to this necessary modification step, the vectors described in the prior art retain other drawbacks which limit their exploitation in gene therapy, and in particular risks of recombination with wild-type adenoviruses. The present invention provides an advantageous solution to this problem.

The present invention consists, in effect, in using recombinant adenoviruses of animal origin for gene therapy in humans. The present invention is the outcome of the demonstration that adenoviruses of animal origin are capable of infecting human cells very effectively. The invention is also based on the demonstration that adenoviruses of animal origin are incapable of propagating in the human cells in which they have been tested. Lastly, the invention is based on the surprising discovery that adenoviruses of animal origin are in no way trans-complemented by adenoviruses of human origin, thereby eliminating all risk of recombination and propagation in vivo in the presence of a human adenovirus, capable of leading to the formation of an infectious particle. The vectors of the invention are hence especially advantageous since the risks inherent in the use of viruses as vectors in gene therapy, such as pathogenicity, transmission, replication, recombination, and the like, are greatly reduced or even abolished.

The present invention thus provides viral vectors which are especially suitable for the transfer and/or expression of desired DNA sequences in humans.

A first subject of the present invention hence relates to the use of a recombinant adenovirus of animal origin containing a heterologous DNA sequence for the preparation of a pharmaceutical composition intended for the therapeutic and/or surgical treatment of the human body.

Adenoviruses of animal origin which are usable in the context of the present invention may be of diverse origins, with the exception of human adenoviruses. Human adenoviruses are those which are naturally infectious in man, generally designated by the term HAd or Ad.

In particular, the adenoviruses of animal origin which are usable in the context of the present invention may be of canine, bovine, murine (example: Mav1, Beard et al., Virology 75 (1990) 81), ovine, porcine, avian or alternatively simian (example: SAV) origin.

More especially, among avian adenoviruses, there may be mentioned the serotypes 1 to 10 which are available in the ATCC, such as, for example, the strains Phelps (ATCC VR-432), Fontes (ATCC VR-280), P7-A (ATCC VR-827), IBH-2A (ATCC VR-828), J2-A (ATCC VR-829), T8-A (ATCC VR-830), K-11 (ATCC VR-921), or alternatively the strains referenced ATCC VR-831 to 835. Among bovine adenoviruses, the different known serotypes may be used, and in particular those available in the ATCC (types 1 to 8) under the references ATCC VR-313, 314, 639–642, 768 and 769. There may also be mentioned murine adenoviruses FL (ATCC VR-550) and E20308 (ATCC VR-528), ovine adenovirus type 5 (ATCC VR-1343) or type 6 (ATCC VR-1340); porcine adenovirus 5359), or simian adenoviruses such as, in particular, the adenoviruses referenced in the ATCC under the numbers VR-591–594, 941–943, 195–203, and the like.

In the context of the invention, it is preferable to use adenoviruses of canine origin, and in particular all strains of CAV2 adenoviruses [strain manhattan or A26/61 (ATCC VR-800), for example]. Canine adenoviruses have formed the subject of many structural studies. Thus, complete restriction maps of CAV1 and CAV2 adenoviruses have been described in the prior art (Spibey et al., J. Gen. Virol. 70 (1989) 165), and the E1a and E3 genes as well as the ITR sequences have been cloned and sequenced (see, in particular, Spibey et al., Virus Res. 14 (1989) 241; Linné, Virus Res. 23 (1992) 119, WO 91/11525). Moreover, canine adenoviruses have already been used for the preparation of vaccines intended for immunizing dogs against rabies, parvoviruses, and the like (WO 91/11525). However, hitherto, the possibility of using these adenoviruses for gene therapy in humans has never been suggested in the prior art. Furthermore, the advantages of such a use had never been weighed up.

The adenoviruses used in the context of the invention should preferably be defective, that is to say incapable of propagating autonomously in the body in which they are administered. As mentioned above, the Applicant has shown that adenoviruses of animal origin are capable of infecting human cells but not of propagating therein. In this sense, they are hence naturally defective in humans and, in contrast to the use of human adenoviruses, do not require genetic modification in this connection. However, the defective character of these adenoviruses may be amplified by genetic modifications of the genome, and in particular by modification of the sequences needed for replication of the said virus in cells. These regions may be either removed (wholly or partially), or rendered non-functional, or modified by insertion of other sequences, and in particular of the heterologous DNA sequence.

Depending on the origin of the adenovirus, the sequences needed for replication can vary somewhat. Nevertheless, they are generally localized close to the ends of the genome. Thus, in the case of CAV-2, the E1a region has been identified, cloned and sequenced (Spibey et al., Virus Res. 14 (1989) 241). It is located on the 2-kb fragment at the left-hand end of the adenovirus genome.

Moreover, other genetic modifications may be performed on these adenoviruses, in particular in order to avoid the production of viral proteins which are undesirable in humans, to permit the insertion of large heterologous DNA sequences and/or to insert particular regions of the genome of another animal or human adenovirus (example: E3 gene).

For the purpose of the present invention, the term "heterologous DNA sequence" denotes any DNA sequence introduced into the virus, the transfer and/or expression of which in humans is desired.

In particular, the heterologous DNA sequence can contain one or more therapeutic genes and/or one or more genes coding for antigenic peptides.

In a particular embodiment, the invention hence relates more especially to the use of adenoviruses of animal origin for the preparation of pharmaceutical compositions intended for the transfer of therapeutic genes in humans. The therapeutic genes which may be transferred in this way are any gene, the transcription and, where appropriate, translation of which in the target cell generate products having a therapeutic effect.

They can be, in particular, genes coding for proteinaceous products having a therapeutic effect. The proteinaceous product thus encoded can be a protein, a peptide, an amino acid, and the like. This proteinaceous product can be homologous with respect to the target cell (that is to say a product which is normally expressed in the target cell when the latter does not display any pathology). In this case, the expression of a protein makes it possible, for example, to compensate for an insufficient expression in the cell or for the expression of a protein that is inactive or poorly active as a result of a modification, or alternatively to overexpress the said protein. The therapeutic gene can also code for a mutant of a cellular protein, having enhanced stability, modified activity, and the like. The proteinaceous product can also be heterologous with respect to the target cell. In this case, an expressed protein can, for example, supplement or supply an activity which is deficient in the cell, enabling it to combat a pathology.

Among products which are therapeutic for the purpose of the present invention, there may be mentioned, more especially, enzymes, blood derivatives, hormones, lymphokines, namely interleukins, interferons, and the like (FR 92/03120), growth factors, neurotransmitters or their precursors or synthetic enzymes, trophic factors, namely BDNF, CNTF, NGF, IGF, GMF, aFGF, bFGF, NT3, NT5, and the like; apolipoproteins, namely ApoAI, ApoAIV, ApoE, and the like (FR 93/05125), dystrophin or a minidystrophin (FR 91/11947), tumour-suppressing genes, namely p53, Rb, Rap1A, DCC, k-rev, and the like (FR 93/04745) and genes coding for factors involved in coagulation, namely factors VII, VIII, IX, and the like.

The therapeutic gene can also be an antisense gene or sequence, expression of which in the target cell enables the expression of cellular genes or the transcription of cellular mRNA to be controlled. Such sequences can, for example, be transcribed in the target cell to RNA complementary to cellular mRNA, and can thus block their translation to protein, according to the technique described in Patent EP 140,308.

As mentioned above, the heterologous DNA sequence can also contain one or more genes coding for an antigenic peptide capable of generating an immune response in humans. In this particular embodiment, the invention hence makes it possible to produce vaccines enabling humans to be immunized, in particular against microorganisms or viruses. Such antigenic peptides can be, in particular, specific to the Epstein-Barr virus, the hepatitis B virus (EP 185,573) or the pseudorabies virus, or alternatively tumour-specific (EP 259,212).

Generally, the heterologous DNA sequence also comprises sequences permitting expression of the therapeutic gene and/or of the gene coding for the antigenic peptide in the infected cell. Such sequences can be the ones which are naturally responsible for expression of the gene in question when these sequences are capable of functioning in the infected cell. They can also be sequences of different origin (responsible for the expression of other proteins, or even synthetic). In particular, they can be promoter sequences of eukaroytic or viral genes. For example, they can be promoter sequences originating from the genome of the cell which it is desired to infect. Similarly, they can be promoter sequences originating from the genome of a virus, including the adenovirus used. The promoters of the E1A, MLP, CMV, RSV, and the like, genes may be mentioned, for example, in this connection. In addition, these expression sequences may be modified by the addition of activating, regulating, and the like, sequences. Moreover, when the inserted gene does not contain expression sequences, it may be inserted into the genome of the defective virus downstream of such a sequence.

Moreover, the heterologous DNA sequence can also contain, especially upstream of the therapeutic gene, a signal sequence directing the synthesized therapeutic product into the pathways of secretion of the target cell. This signal sequence can be the natural signal sequence of the therapeutic product, but it can also be any other functional signal sequence or an artificial signal sequence.

The defective adenoviruses according to the invention may be prepared by any technique known to a person skilled in the art. In particular, they may be prepared according to the protocol described in application WO 91/11525. The traditional preparation technique is based on homologous recombination between an animal adenovirus and a plasmid carrying, inter alia, the heterologous DNA sequence which it is desired to insert. Homologous recombination takes place after cotransfection of the said adenovirus and plasmid into a suitable cell line. The cell line used should preferably be transformable by the said elements and, in the case where a modified adenovirus of animal origin is used, the cell line can, if necessary, contain sequences capable of complementing the portion of the defective adenovirus genome, preferably in integrated form in order to avoid risks of recombination. As an example of a line, the GHK greyhound kidney cell line (Flow laboratories) or the MDCK cell line may be mentioned. The conditions of culture of cells and of preparation of the viruses or of the viral DNA have also been described in the literature (see, in particular, Macatney et al., Science 44 (1988) 9; Fowlkes et al., J. Mol. Biol. 132 (1979) 163).

Thereafter, the vectors which have multiplied are recovered and purified according to the traditional techniques of molecular biology.

Another subject of the present invention consists of a recombinant adenovirus of animal origin containing a heterologous DNA sequence comprising at least one therapeutic gene as defined above.

The subject of the invention is also any pharmaceutical composition containing a recombinant adenovirus of animal origin as defined above. The pharmaceutical compositions of the invention may be formulated with a view to topical, oral, parenteral, intranasal, intravenous, intramuscular, subcutaneous, intraocular, and the like, administration.

Preferably, the pharmaceutical composition contains vehicles which are pharmaceutically acceptable for an injectable formulation. These can be, in particular, sterile, isotonic saline solutions (monosodium or disodium phosphate, sodium, potassium, calcium or magnesium chloride, and the like, or mixtures of such salts), or dry, in particular lyophilized, compositions which, on adding sterilized water or physiological saline, as the case may be, enable injectable solutions to be formed.

The doses of virus used for the injection may be adapted in accordance with different parameters, and in particular in accordance with the mode of administration used, the pathology in question, the gene to be expressed or the desired period of treatment. Generally speaking, the recombinant adenoviruses according to the invention are formulated and administered in the form of doses of between $10^4$ and $10^{14}$ pfu/ml, and preferably $10^6$ to $10^{10}$ pfu/ml. The term pfu (plaque forming unit) corresponds to the infectious power of a solution of virus, and is determined by infecting a suitable cell culture and measuring, generally after 5 days, the number of plaques of infected cells. The techniques of determination of the pfu titre of a viral solution are well documented in the literature.

Depending on the heterologous DNA sequence inserted, the adenoviruses of the invention may be used for the treatment or prevention of a large number of pathologies, including genetic diseases (dystrophy, cystic fibrosis, and the like), neurodegenerative diseases (Alzheimer's, Parkinson's, ALS, and the like), cancers, pathologies associated with disorders of coagulation or with dislipoproteinaemias, pathologies associated with viral infections (hepatitis, AIDS, and the like), and the like.

The present invention will be described more completely by means of the examples which follow, which should be considered to be illustrative and non-limiting.

LEGENDS TO THE FIGURES

FIG. 1: Restriction map of the CAV2 adenovirus strain Manhattan (according to Spibey et al., cited above).

Figures 2, 2A:
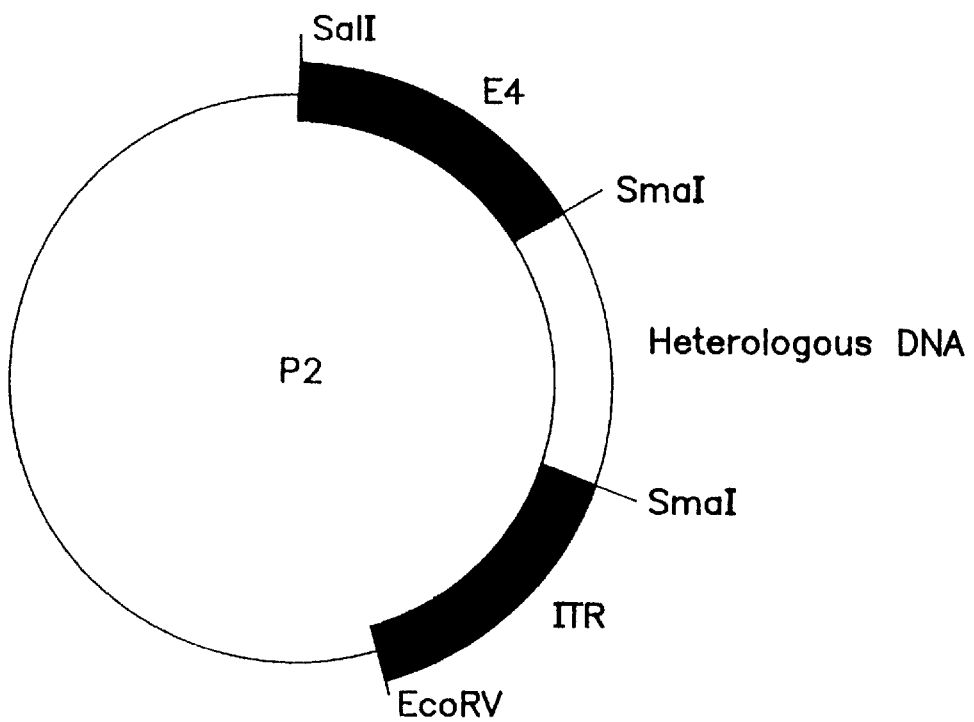
Figure 2B:
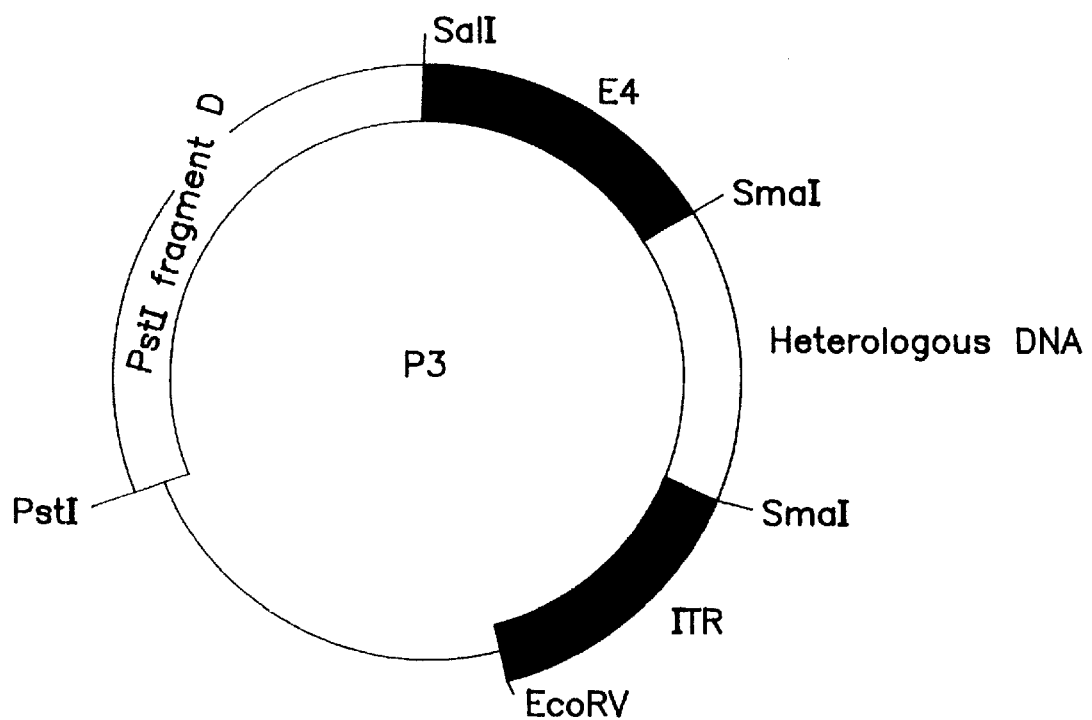

FIGS. 2a and 2b: Map of plasmids p1, p2 (FIG. 2a) and p3 (FIG. 2b).

Figure 3A:
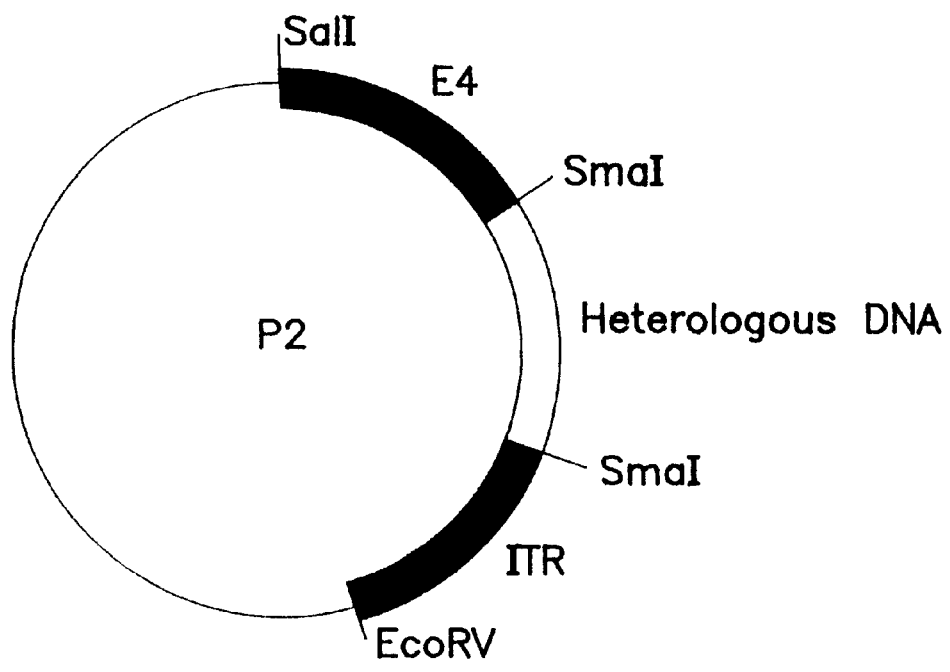
Figure 3A:
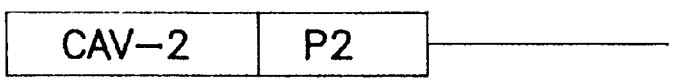
Figure 3B:
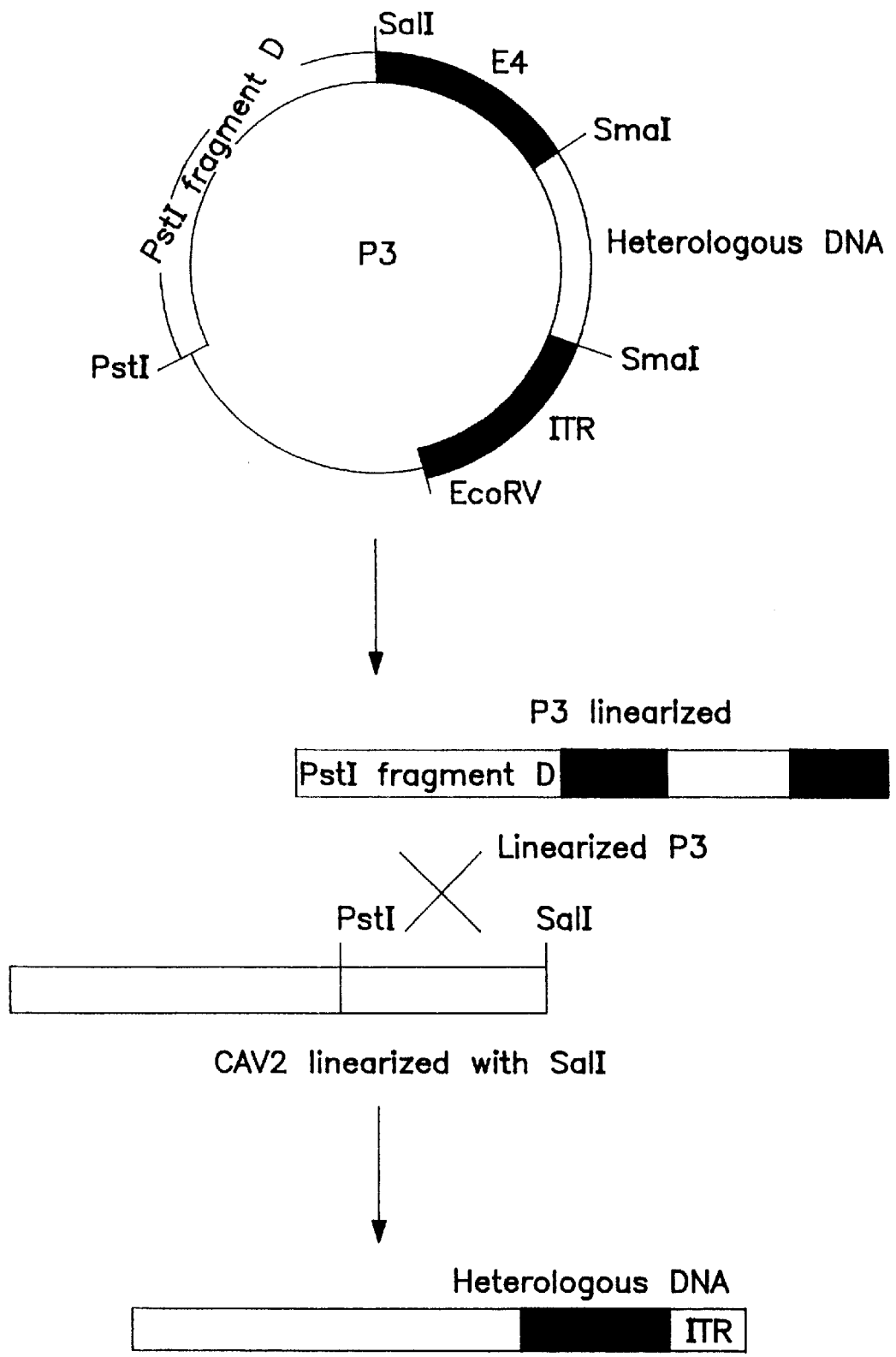

FIGS. 3a and 3b: Strategy for the construction of a recombinant canine adenovirus containing a heterologous DNA sequence.

GENERAL TECHNIQUES OF MOLECULAR BIOLOGY

The methods traditionally used in molecular biology, such as preparative extractions of plasmid DNA, centrifugation of plasmid DNA in a caesium chloride gradient, agarose or acrylamide gel electrophoresis, purification of DNA fragments by electroelution, phenol or phenol-chloroform extraction of proteins, ethanol or isopropanol precipitation of DNA in a saline medium, transformation in Escherichia coli, and the like, are well known to a person skilled in the art and are amply described in the literature [Maniatis T. et al., "Molecular Cloning, a Laboratory Manual", Cold Spring Harbor Laboratory, Cold Spring Harbor, N.Y., 1982; Ausubel F. M. et al. (eds), "Current Protocols in Molecular Biology", John Wiley & Sons, New York, 1987].

Plasmids of the pBR322 and pUC type and phages of the M13 series are of commercial origin (Bethesda Research Laboratories).

To carry out ligation, the DNA fragments may be separated according to their size by agarose or acrylamide gel electrophoresis, extracted with phenol or with a phenol-chloroform mixture, precipitated with ethanol and then incubated in the presence of phage T4 DNA ligase (Biolabs) according to the supplier's recommendations.

The filling in of 5' protruding ends may be performed with the Klenow fragment of E.coli DNA polymerase I (Biolabs) according to the supplier's specifications. The destruction of 3' protruding ends is performed in the presence of phage T4 DNA polymerase (Biolabs) used according to the manufacturer's recommendations. The destruction of 5' protruding ends is performed by a controlled treatment with S1 nuclease.

Mutagenesis directed in vitro by synthetic oligodeoxynucleotides may be performed according to the method according to Taylor et al. [Nucleic Acids Res. 13 (1985) 8749–8764] using the kit distributed by Amersham.

The enzymatic amplification of DNA fragments by the so-called PCR [Polymerase-catalysed Chain Reaction, Saiki R. K. et al., Science 230 (1985) 1350–1354; Mullis K. B. and Faloona F. A., Meth. Enzym. 155 (1987) 335–350] technique may be performed using a DNA thermal cycler (Perkin Elmer Cetus) according to the manufacturer's specifications.

The verification of the nucleotide sequences may be performed by the method developed by Sanger et al. [Proc. Natl. Acad. Sci. USA, 74 (1977) 5463–5467] using the kit distributed by Amersham.

EXAMPLES

E1. Infection of Human Cells with Adenoviruses of Canine Origin

This example demonstrates the capacity of adenoviruses of animal (canine) origin to infect human cells.

E1.1. Cell lines used

In this example, the following cell lines were used:

Human embryonic kidney line 293 (Graham et al., J. Gen. Virol. 36 (1977) 59). This line contains, in particular, integrated in its genome, the left-hand portion of the Ad5 human adenovirus genome(12%).

KB human cell line: Originating from a human epidermal carcinoma, this line is available in the ATCC (ref. CCL17), together with the conditions enabling it to be cultured.

Hela human cell line: Originating from a human epithelial carcinoma, this line is available in the ATCC (ref. CCL2), together with the conditions enabling it to be cultured.

MDCK canine cell line: The conditions of culture of MDCK cells have been described, in particular, by Macatney et al., Science 44 (1988) 9.

E1.2. Infection

Cells of the cell lines mentioned above are infected with CAV2 virus (strain Manhattan). For this purpose, the cells (approximately $10^7$/dish) were incubated for 1 hour at 37° C. in the presence of 10 pfu/cell of virus. 5 ml of culture medium were then added and culturing was continued at 37° C. for approximately 48 hours. At this point, the DNA present in episomal form in the infected cells was analysed: the results obtained show that all the cell lines possess CAV2 DNA in their nuclei, thereby demonstrating that they can be infected by canine adenoviruses.

E2. Absence of Propagation of Adenoviruses of Canine Origin in Human Cells

This example demonstrates that canine adenoviruses, although capable of infecting human cells, do not propagate therein.

After infection of cells according to Example 1, the quantity of CAV2 DNA was assayed over time according to the following protocol: the episomal DNA present in the cells was recovered according to the technique described by Hirt et al. (J. Virol. 45 (1983) 91), and the quantity of DNA was assayed by comparison with a standard series. The results obtained show that the quantity of viral DNA does not increase in KB and 293 cells, demonstrating a complete absence of replication of CAV2 in these cells. In MDCK and Hela cells, a slight increase in the quantity of CAV2 viral DNA is observed. However, assay of the formation of viral particles shows that no propagation of CAV2 takes place in 293, KB and Hela human cells, only in the MDCK canine line. Propagation was measured by harvesting the infected cells, releasing any viruses by freezing/thawing and infecting MDCK cells with the supernatant thereby obtained, under the conditions described above. After 48 hours of culture, the absence of viral DNA in MDCK cells infected in this manner demonstrates that no viral propagation has taken place in the human cells.

These results show clearly that canine adenoviruses are incapable of propagating in human cells.

E3. Demonstration of the Absence of Trans-complementation of Canine Adenoviruses by Human Adenoviruses This example shows that the absence of propagation of canine adenoviruses in human cells is not trans-complemented by the presence of human adenoviruses.

Cells of the 293, KB and Hela human lines and of the MDCK canine line were coinfected with CAV2 adenovirus and Ad5 human adenovirus. The presence of viral (canine and human) DNA in the cells was demonstrated as in Example E1, and the quantity of DNA was assayed over time, together with propagation. The results obtained show that the quantity of CAV2 DNA does not increase over time in KB and 293 cells, thereby demonstrating that the presence of Ad5 human adenovirus does not induce replication of CAV2 in these cells by trans-complementation. The absence of viral DNA in the MDCK cells infected with the possible viruses originating from the KB, 293 and Hela cells likewise demonstrates that no propagation of the CAV2 adenovirus in the human cell lines has taken place, even in the presence of human adenovirus.

E4. Construction of a CAV2 Genomic DNA Library

A library of plasmids was constructed from restriction fragments of the CAV2 adenovirus genome. This library was obtained by digestion of CAV2 with the enzymes SmaI and PstI and cloning of the SmaI fragments, namely A, B, C, D, E, F, I and J, and PstI fragments, namely A, B, C, D, E, F, G and H (FIG. 1) into the vector pGem3Zf+ (Promega). The plasmid carrying the SmaI fragment C was then cotransfected into MDCK cells with plasmid pUC4KIXX (Pharmacia) carrying the neomycin resistance gene, to establish an MDCK line constitutively expressing the E1A and E1B genes of CAV2. This line permits the construction of recombinant viruses from which these regions have been deleted (see E5.2.).

E5. Construction of Recombinant Canine Adenoviruses Carrying the Interleukin-2 Gene Under the Control of the MLP Promoter of Ad2.

Two strategies for the construction of recombinant canine adenoviruses carrying the interleukin-2 gene under the control of the MLP promoter of human Ad2 were devised.

E5.1. The first consists in inserting the desired heterologous DNA sequence (MLP promoter-interleukin-2 gene) between the E4 region and the right-hand ITR of the entire CAV2 genome at the SmaI restriction site. The construction of such a recombinant is performed either by ligation, or by in vivo recombination between a plasmid carrying the desired heterologous DNA sequence and the CAV2 genome. The plasmids used for obtaining the recombinant adenoviruses carrying the interleukin-2 gene under the control of the MLP promoter are constructed in the following manner (FIG. 2):

a first plasmid, designated p1, is obtained by cloning the SalI fragment B of CAV2 (FIG. 1), containing, in particular, the right-hand ITR, a SmaI site and the E4 gene, into plasmid pGem3Zf+ (Promega); the SmaI site is unique on p1;

the heterologous DNA sequence (MLP promoter-interleukin-2 gene) is introduced at the SmaI site of plasmid p1 to generate plasmid p2; and the PstI-SalI fragment contained in the PstI fragment D of the genomic library and carrying a portion of the E3 gene is then cloned at the corresponding site in p2 to generate plasmid p3 (FIG. 2).

The plasmids thereby obtained are used to prepare the recombinant adenoviruses according to the following two protocols (see FIG. 3):

a) in vitro ligation of plasmid p2 digested with SalI to the SalI fragment A of CAV2, and transfection of the ligation product into MDCK cells (FIG. 3a), b) Recombination between plasmid p3 and the SalI fragment A of CAV2 after cotransfection into MDCK cells (FIG. 3b). The recombinant adenoviruses obtained are then isolated and amplified according to techniques known to a person skilled in the art.

These manipulations permit the construction of recombinant canine adenoviruses carrying the interleukin-2 gene, which are usable for the transfer of this therapeutic gene in man (FIG. 3).

E5.2. The second strategy devised is based on the use of MDCK cell line constitutively expressing the E1A and E1B genes of CAV2 (see Example E4). This line permits, in effect, trans-complementation of canine adenoviruses from which these regions have been deleted, and thus the construction of recombinant viruses in which the heterologous DNA sequence is substituted for the E1 region. For this purpose, a plasmid containing the left-hand end (ITR sequence and encapsidation sequence) of the CAV2 genome and the heterologous DNA sequence is constructed. This plasmid is cotransfected into the MDCK cells described above, in the presence of the genome of a CAV2 adenovirus from which its own left-hand end has been deleted. The recombinant canine adenoviruses produced are recovered, where appropriate amplified and stored for the purpose of using them in humans.

What is claimed is:

1. A recombinant canine CAV-2 adenovirus, comprising at least one inserted human gene and sequences permitting expression of the inserted gene in a human cell in which the recombinant adenovirus is infectious.

2. The adenovirus according to claim 1, wherein the gene encodes a protein selected from the group consisting of an enzyme, a hormone, a lymphokine, a growth factor, a trophic factor, an apolipoprotein, a dystrophin, a minidystrophin, a tumour-suppressor, and a coagulation factor.

3. The adenovirus according to claim 1, further comprising sequences encoding a signal sequence enabling secretion of an encoded protein of the inserted human gene.

4. The adenovirus according to claim 1, wherein the product of the inserted gene is an antisense sequence.

5. The adenovirus according to claim 1, wherein its genome lacks the E1 region.

6. The adenovirus according to claim 5, comprising a region of another animal or human adenovirus genome.

* * * * *